US007171426B2

(12) United States Patent
Farmer et al.

(10) Patent No.: US 7,171,426 B2
(45) Date of Patent: *Jan. 30, 2007

(54) HAZARD COMMUNICATION SYSTEM

(75) Inventors: Janice Lynn Farmer, Humble, TX (US); Patsy Mask Hill, Kingwood, TX (US); Greg P. Dietz, McLean, VA (US); Gertrude Companion, Houston, TX (US); David A. Cogar, Falls Church, VA (US); Matthew C. Finkelstein, Washington, DC (US); Edmund L. Dickson, Sacramento, CA (US); Joe Wix, Missouri City, TX (US); Barbara A. Stevens, Kingwood, TX (US)

(73) Assignee: Shell Oil Company, Houston, TX (US)

( * ) Notice: Subject to any disclaimer, the term of this patent is extended or adjusted under 35 U.S.C. 154(b) by 517 days.

This patent is subject to a terminal disclaimer.

(21) Appl. No.: 09/306,135

(22) Filed: May 6, 1999

(65) Prior Publication Data

US 2003/0004965 A1    Jan. 2, 2003

Related U.S. Application Data

(60) Provisional application No. 60/085,110, filed on May 12, 1998.

(51) Int. Cl.
  *G06F 17/30* (2006.01)
(52) U.S. Cl. .................. 707/104.1; 707/101; 707/102; 705/1; 705/9; 705/28; 700/102; 700/106
(58) Field of Classification Search .............. 707/104, 707/104.1, 100, 101, 102; 705/1, 9, 28; 700/96, 700/102, 106
  See application file for complete search history.

(56) References Cited

U.S. PATENT DOCUMENTS

| 4,347,568 | A | 8/1982 | Giguere et al. ............. 600/300 |
| 5,191,522 | A | 3/1993 | Bosco et al. .................... 705/4 |
| 5,218,669 | A | 6/1993 | Kobayashi et al. ........... 706/47 |
| 5,303,332 | A | 4/1994 | Kirk et al. ..................... 706/50 |

(Continued)

FOREIGN PATENT DOCUMENTS

| GB | 2225138 | 5/1990 |
| JP | 07175791 | 7/1995 |

OTHER PUBLICATIONS

US Department of Labor, "Interpretation on whether "an equivalent electronic electronic information system" could be used in lieu of MSDSs to satisfy the HCS", http.//www.osha.gov, Jul. 6, 1990, pp. 1-8.*

(Continued)

*Primary Examiner*—Khanh B. Pham

(57) ABSTRACT

The invention is an integrated, data-centric hazard communication system. The system has an authoring module and a means for disseminating hazard information about a material and its components, decomposition products and related materials. The authoring module decompiles material data, associates the decompiled data with hazard information, and recompiles material data associated with hazard information to provide hazard information about the material, its components, decomposition products of the material, and substances related to the material. The system can be a general purpose computer programmed with computer instructions to perform these functions. Computer software for performing these functions is also presented.

22 Claims, 4 Drawing Sheets

U.S. PATENT DOCUMENTS

| | | | | |
|---|---|---|---|---|
| 5,311,438 A | * | 5/1994 | Sellers et al. | 700/96 |
| 5,446,653 A | | 8/1995 | Miller et al. | 705/4 |
| 5,446,885 A | | 8/1995 | Moore et al. | 707/103 R |
| 5,537,590 A | | 7/1996 | Amado | 707/2 |
| 5,596,752 A | | 1/1997 | Knudsen et al. | 717/117 |
| 5,630,127 A | | 5/1997 | Moore et al. | 707/103 R |
| 5,664,112 A | | 9/1997 | Sturgeon et al. | 705/28 |
| 5,712,990 A | * | 1/1998 | Henderson | 705/28 |
| 5,724,255 A | | 3/1998 | Smith et al. | 364/500 |
| 5,726,884 A | * | 3/1998 | Sturgeon et al. | 705/9 |
| 6,097,995 A | * | 8/2000 | Tipton et al. | 700/266 |
| 6,122,622 A | * | 9/2000 | Wiitala et al. | 705/28 |
| 6,163,732 A | * | 12/2000 | Petke et al. | 700/106 |
| 6,167,394 A | * | 12/2000 | Leung et al. | 707/3 |
| 6,341,287 B1 | * | 1/2002 | Sziklai et al. | 707/102 |

OTHER PUBLICATIONS

U.S Department of Labor, "MSDS Requirements", Http://www.osha.gov, May 7, 1993, pp. 1-3.*

U.S Department of Labor, "Maintaining MSDSs On a Computer Data Base", http://www.osha.gov, Jan. 13, 1986, pp. 1-3.*

U.S Department of Labor, "Hazard Communication Standard", Http://www.osha.gov, Jan. 1, 1993, pp. 1-3.*

Material Eng. Lab, Naval Aviation Depot, San Diego, CA, USA, Journal of Testing Evaluation, vol. 25, No. 3, pp. 341-348, May 1997.

LHASA UK Ltd., Leeds Univ., UK, Journal of Chemical Information & Computer Sciences, vol. 37, No. 1, pp. 148-150, Jan. 2, 1997.

Research Disclosure-346042, Published Feb. 1993, Rule-Book Processing.

Research Disclosure-346036, Published Feb. 1993, Execution of Multiple Branches of Rules.

Prosar Vendor MSDS Management by Prosar Product Safety Resources 1998.

MSDS Software Report by Donley Technology, 1997.

* cited by examiner

*TECHNICAL ARCHITECTURE*

HAZARD COMMUNICATION SYSTEM

This application claims the benefit of U.S. Provisional Application No. 60/085,110 filed May 12, 1998, the entire disclosure of which is hereby incorporated by reference.

BACKGROUND OF THE INVENTION

This invention relates to the automated and integrated management of health, safety and environmental information as it pertains to the manufacture, use, handling, transport, and sales of chemical products.

The invention is useful in light of the widely regulated nature of these activities. Federal and State laws and regulations such as the Occupational Safety and Health Act ("OSHA") have much to say about the information that must be gathered, maintained, stored, evaluated and distributed in chemical manufacturing. For example, the regulations require an employer to establish a written hazard communication plan to advise its employees of hazards associated with chemicals the employees handle, and incorporate into this plan the use of container labels, warning signs, Material Safety Data Sheets ("MSDSs") and training programs. The centerpiece of the OSHA Hazard Communication Standard is the MSDS, required for each hazardous substance manufactured or used on the site. The MSDS includes all relevant information pertaining to a hazardous substance, from its ingredients to physical properties, health hazards, exposure limits, regulatory controls, storage incompatibilities, safe handling and use precautions and much more.

This and other legislation, with its demanding regulatory requirements, has created a need for sophisticated information management solutions to assist industry and other impacted entities in the compliance process. In recent years, software applications have emerged that attempt to manage selected aspects of compliance, such as dissemination of MSDS or Hazardous Waste Manifest information. Most solutions have been of a limited scope.

For example, the FLOW GEMINI program previously available from General Research provides hazardous substance report generation, using a blank screen on which the user designs the reporting forms to be used. Some standard report forms are included with this software.

SAP produces a software module that can be used to gather chemical data into a substance database and allows users to manually select phrases for MSDS construction. It does not involve an automated rule-driven process for generating hazard information about the materials.

Imagetrak Software's MSDS ExPress allows scanning of MSDS images, which are then attached in an unspecified way to a database record. Information contained on the scanned-in MSDSs can then be queried in a simple question and answer format.

OSHA-SOFT's Compliance Manager provides a link between MSDSs and chemical inventory information, to facilitate compliance with the OSHA Hazards Communication Standard.

U.S. Pat. No. 5,664,112 to Alternative Systems, Inc. proposes a hazard communication system containing some of the elements outlined above but includes and integrates modules for tracking waste spills and inventory as well as several other informational elements.

The systems of the prior art combine product information entered by a system user with document templates to create hazard communication documents. That is to say, MSDS authoring has largely been document-based. Data was compiled from a variety of sources and scanned or manually entered into forms or precursors of forms such as electronic document templates. Each time a data element changed, all of the documents based on the data needed to be called up and revised individually. In some cases this was done by directly associating product data with document data fields. In other cases it is done through a relational database which arrived at the same result indirectly. Prior art systems have not presented a means for decompiling information about a material, associating hazard information with the decompiled information, and then recompiling hazard communications based upon a systematic application of rules. Instead, the system user provided all of the data about each substance for which a document was to be prepared. No systemic means have heretofore been available to create and disseminate hazard data for components of substances or substances derived or related to them.

SUMMARY OF THE INVENTION

The invention is an integrated, data-centric hazard communication system comprising an authoring module and a means for disseminating hazard information about a material and its components, decomposition products and related materials. Within the authoring module there is a means for decompiling material data, a means for associating the decompiled data with hazard information, and a means for recompiling material data associated with hazard information to provide hazard information about the material, its components, decomposition products of the material, and substances related to the material. The authoring module comprises a deblending analyzer; a substance processor; a rules engine for generating words and phrases used in the production of documents and system output; and a document generator for producing documents to disseminate the hazard information. The distribution module disseminates the documents created in the authoring module.

In one embodiment of the invention, an apparatus comprising the hazard communication system is presented.

In another embodiment of the invention, a process is presented for communicating hazards associated with chemical substances. The process comprises the steps of creating a hazard communication document by entering material information into the system; processing entered information through an authoring module where hazard information is decompiled, associated with the material information, recompiled to provide hazard information about the material, its components, decomposition products of the material, and substances related to the material; and disseminating such hazard information.

In a further embodiment of the invention the hazard communication system is computer software which drives a general purpose computer to perform the steps of the process referred to above.

DETAILED DESCRIPTION OF THE INVENTION

Figure 1:
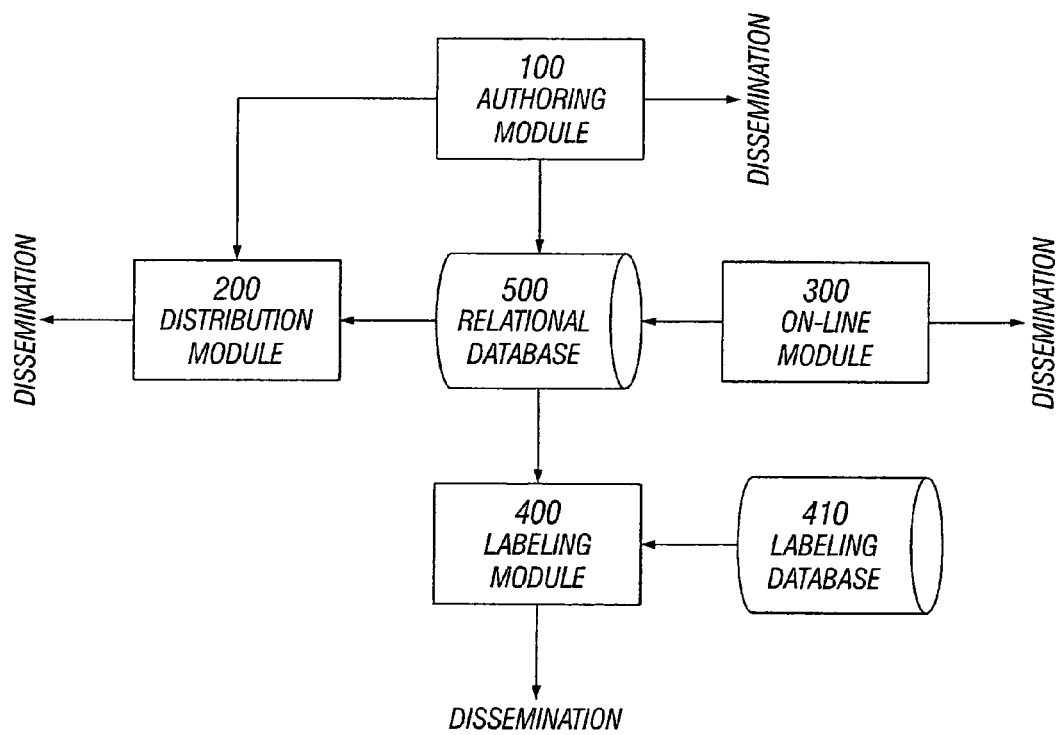
FIG. 1 is a schematic view of a Hazard Communication System according to the invention.

FIG. 1 provides a schematic overview of a hazard communication system of this invention. It is organized into four modules in one embodiment: authoring module 100, optional distribution module 200, optional on-line module 300 and optional labeling module 400. A relational database schema or database design 500, links and fuses the modules into a single, integrated entity. The system is best operated in a client-server computer configuration in which the programs for operating the modules are programmed into one or more application servers on magnetic, optical, magneto-optical, or other medium useful for storing and communicating instructions and data to computer/computer-operated systems. Further, one of ordinary skill in the art will recognize that while each of the events or steps described in this specification may be presented as a process, once a computer or computing device is programmed to conduct these processes, the device and program comprise an apparatus or article for conducting theses processes. Well known computer languages such as C++, SQL, POWERBUILDER, Visual Basic, and Java languages are useful for this purpose.

The authoring module 100 provides the material information management foundation of the invention. It is the point at which information about a material is initially entered into the system and manages and tracks information about materials, whether these materials are pure chemicals (i.e., elements, molecules, compounds, and complexes which are not mixtures) or, mixtures/blends of chemicals, or mixtures of mixtures. Within the authoring module 100, pure chemicals and mixtures are profiled according to their chemical names and synonyms, physical and chemical properties, health effect hazards, environmental toxicology, regulatory classifications, transportation, and employee protection. These profiles are then used to associate hazard communication information with the material for communication to anyone having a need for such information.

Through the authoring module 100, the user defines all materials for which a record is to be made. Information used to populate the authoring module is entered into the system through interactive computer screens, dialogue boxes, or import procedures. Data is stored and referenced as material records described more fully below. Structuring the authoring module of this invention as described herein allows documents for many different regulatory authorities, languages, business needs, and users to be written from only one review of the data.

Once data is entered, the material record comprised of that data is stored in data tables associated with one or more relational databases 500. While FIG. 1 shows only one relational database 500, one skilled in the art will appreciate that any number of relational databases may operate independently or together in order to accomplish the functions and processes described throughout this specification. All data relating to a given material and its related materials are linked together by relationships among the relational databases 500. The preferred relational databases of the instant invention are Microsoft SQL Server, Oracle and Sybase SQL Servers. When data change, the relationships among the data components update all records and documentation affected. Thus, only one record needs to be kept for any given material even where the material has numerous trade names and manufacturers.

The data storage model used in the apparatus and process of the preferred embodiment of this invention is based upon a material/class/component record system (hereafter collectively referred to as the "data storage model"). A material record is a complete set of hazard data for a material, a class of materials, or one or more components of a class of materials. A material is one or more chemicals or groups of chemicals with a set of common characteristics such as composition, chemical properties, and physical properties. Hazard information includes the physical and chemical characteristics of a material relevant to regulatory, toxicological, safety (e.g., employee protection), and transportation requirements and the characterization of the material as required or suggested therefrom. A class of materials is an association of materials with similar properties and associated hazard information. A material record for a class comprises a range of data for all of the members of the class ("siblings"). For example, a material class defined as "motor oils" can include siblings "10W" and "20W" motor oils. The authoring module enables all references to a data file and accessing of all data files by material records relating to single materials, classes, components/siblings, and related materials. Thus, when updating data, a user can identify all materials related to the material for which the data is to be updated. This facilitates more rapid and accurate maintenance of hazard information than was previously available in prior art MSDS systems.

System outputs such as on-line (interactive) screen displays and documents are all compiled by retrieving material records and associating them with specific data through the logic of the system. The data storage model of this invention facilitates the assembly of data from a number of material records to create material records for classes and new materials. It also facilitates the quick and ubiquitous change of data and recognition of such changes or the need for such changes by the designation of the record's status (e.g., draft, revision, or final versions).

Once a document is produced in the authoring module 100 is can be passed to an optional distribution module 200. There, hazard documents are identified and distributed based on media requirements, preferred languages, and document types. System users can indicate media requirements, languages, and document types by interactive computer screen displays. For example, the system user can chose to prepare an English-language MSDS or safety bulletin and specify whether it is to be distributed via the Internet, electronic mail, file transfer protocol, a paper copy, via facsimile, or downloaded to a computer diskette or CD-ROM. The distribution module includes a processor to trigger dissemination based on product movements (e.g., sales), regulatory events, and document revisions. When such an event occurs, the appropriate standard document is distributed through the cooperation of the processor and the distribution module 200. For example, the distribution module 200 may contain a statement such as the following: "If the MSDS for product XYZ has been revised Then distribute XYZ MSDS to all purchasers of XYZ in the last three years." The system would then identify the data needed to populate an MSDS, obtain the identified document through communication with relational database 500, and signal the distribution module to send the MSDS sheet. Of course, the system must have appropriate communications devices and connectivity equipment to distribute the documents in the media required. For example, modems, facsimile software, CD-ROM writers, printers, device drivers and other well known associated hardware and software are required to enable the full panoply of distribution options outlined above.

An optional on-line module 300 is used to communicate and distribute hazard information such as MSDS sheets to systems and users by remote communication means such as an Intranet or through the global information infrastructure commonly referred to as the Internet. System users access this module through the use of a web browser. Once they have entered the system through this means the user can indicate preferred languages and document types by interactive computer screen displays. The on-line module 300 retrieves the document that has been requested from the relational database 500 which extracts the appropriate data and provides it back to the on-line module 300. Users search for materials by work area, equipment or by general search. Once a material is identified, the user can view and print hazard documents using the computer screen displays. Within the module, is a file format converter which converts and compiles the data into a data stream in ASCII, HTML, RTF or other format which can be communicated through Intranet or Internet communications channels. The data is communicated to the user over the Intranet or Internet communications channel used.

Optional labeling module 400 is used to generate labels to be attached to products/product packaging to be transported or stored. The user indicates the product, container, label types, and labeling site by interactive computer screen. Labeling module 400 communicates with labeling database 410 to populate label formats with substance information obtained through authoring module 100 and relational database 500. The label format is completed and compiled in labeling module 400 and communicated to the site for which the label will be prepared such as the manufacturing facility or shipment facility. These labeling sites maintain communications hardware and software for receiving and printing the labels communicated to them. For example, the labeling site can maintain one or more personal computers with a local label database and appropriate printers. The label information described above can be entered into the personal computer by, for example, diskette, through a connected network to the labeling module 400, and via Intranet or Internet as described below. The local label database can also ascribe local data to the labels such as product distributor name, facility name, bar coding information, and distribution date. Labels are then produced on local hardware such as label printers through communication with the local label database.

These four modules are integrated by interfaces that share hazard document information between each module. From the database schema 500, common data are created, updated, stored and retrieved within and between the modules and their components. This integration and creation, updating, storage, and retrieval of data and instructions among modules is referred to herein as communication among the modules and processes. The authoring module 100 creates hazard documents for all manufactured products. The resulting documents of the authoring process 100 are sent to the online module 300. The online module 300 stores it own copy of these documents and also stores vendor MSDSs which are imported into the module from external data sources (e.g. key entry, third party data providers). The distribution module 200 receives an index of documents from both the authoring module 100 and the online module 300. When sending documents to customers, the distribution module pulls the documents directly from the authoring module 100 or the online module 300. The labeling module 400 acquires label content and format from the authoring module 100 as a result of the document generation process. Batch processors routinely transmit data between modules, typically on a nightly basis. In this manner, the entire system is synchronized so that MSDS and labels contain common hazard information as soon as revisions are approved during the authoring process 100. The changes can be provided to customers, employees, and packages in the distribution 200, online 300, and labeling 400 modules.

Figure 2:
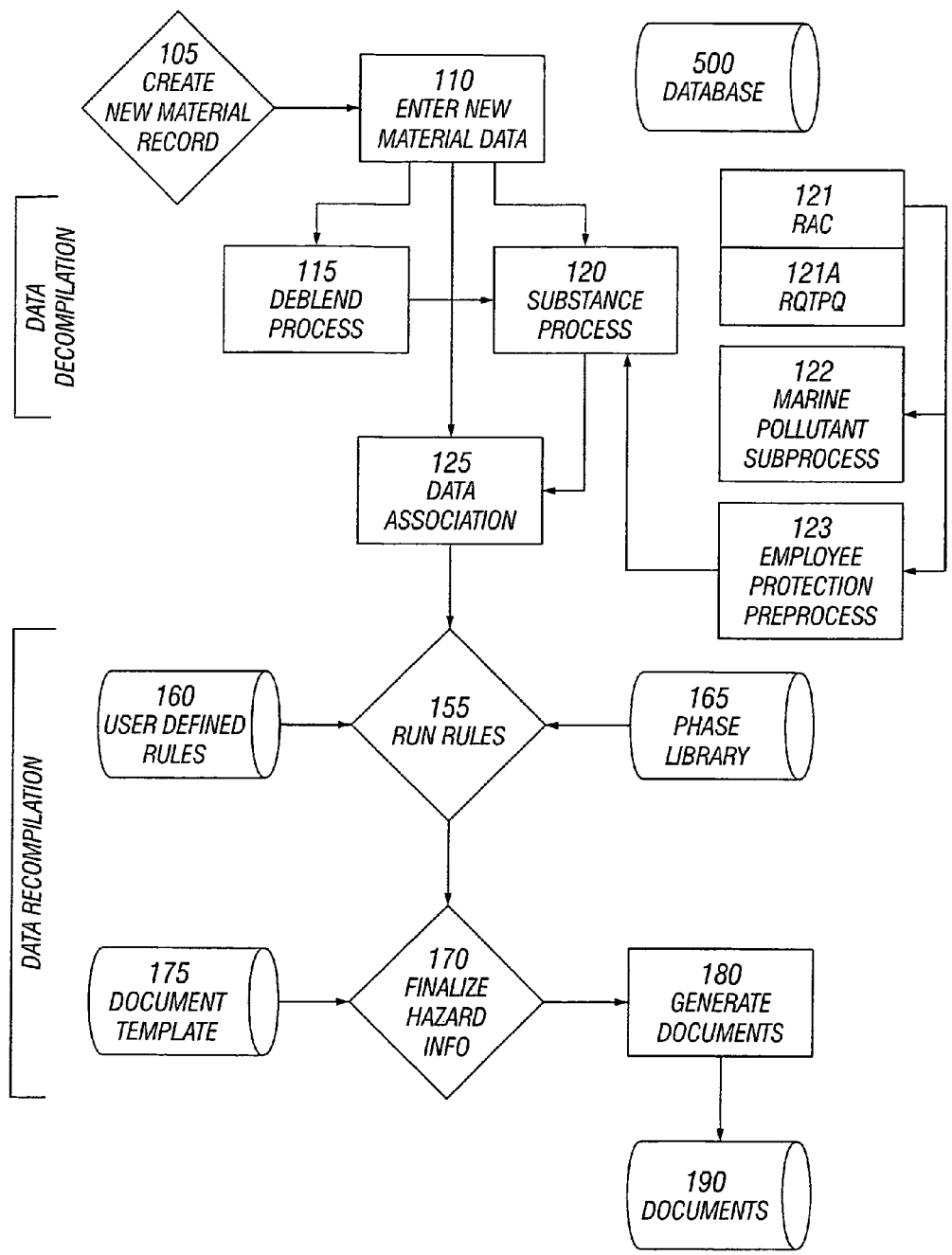
FIG. 2 is a schematic view of the authoring process used in a hazard communication system according to this invention.

The authoring module and the process employed by it can best be understood by reference to FIG. 2. Each of the functions represented in this figure interact with and among one or more databases 500. As data is entered or processed in any step, it populates or updates data tables in the same manner as that described above. This need not occur in one database or any central database. Indeed, each process or function shown or described can have its own database associated with it and still be considered part of database 500.

In step 105, a system user initiates the creation of a new material record. Preferably, this is done through an interactive computer display screen as is commonly done in the field of computer programming.

In step 110, material data is entered, preferably through interactive computer display screens. Four types of data are entered: (1) material information comprising references to the materials such as CAS (Chemical Abstract Services) numbers and synonyms, chemical formula, chemical family, and class member (2) composition information comprising an ingredient list to include minimum, maximum, and typical concentrations of the ingredients, (3) business information comprising product codes, trade names, and producers, and (4) properties of the material, its components and its decomposition products comprising physical state and properties such as Aluminum Concentration, Amine Content, Aniline Point, Antimony Concentration, Appearance, Argon Concentration, Auto Ignition Temperature, Average Molecular Weight, Barium Concentration, Base Amine Value, Bioaccumulation, Bioconcentration, Boiling Point, Bulk Density, Cadmium Concentration, Chromium Concentration, Cobalt Concentration, Color, Consistency, Copper Concentration, Density, Dielectric Strength, Diffusivity, Dissociation Constant, Drop Point, Evaporation Rate, Fat Solubility, Film Strength Durability, Flash Point, Flex Modulus, Flex Strength, Flow Time, Foam, Free Water Content, Freezing Point, Fretting Wear, Gear Wear, Glass Transition Temperature, Half life, Hardness, Heat of Fusion, Heat Value, Henry's Law Constant, Hydrocarbon content, Hydrogen Concentration, Interfacial Tension, Iron Concentration, Lead Concentration, Load Carrying, Lower Dust Explosion Limit, Lower Explosive Limit, Lower Flamability Limit, Manganese Concentration, Melt Index or Melting Point Ra, Melting Point, Mercury, Metal Corrosion, MIR, Mobility, MOIR, Molecular Weight—Daltons, Molecular Weight<1000, Molecular Weight<500, Molybdenum Concentration, Nickel Concentration, Number Molecular Weight, Octanol/Water Partition Coefficient, Odor, Odor Threshold, Oil Content, Organic Carbon Partition Coefficient, Oxidation Stability, Particle Size Distribution 0–20, Particle Size, Particle Size Distribution<x, Penetration Needle, Penetration Unworked, Penetration Worked, pH, Polar, Pour Point, Refractive Index, Rubber Swell, Saturated Vapor Concentration, Selenium Concentration, Shelf Life, Shipping Temperature, Silver Concentration, Softening Point, Soil/Sediment Partition, Solubility (in Water), Solubility (Mac Kay), Solubility (Other), Solvent Separation Test, Solvent/Solids Concentration, Sorption, Specific Gravity, Stability, Static charge, Storage Temperature, Strontium Concentration, Substances not part of the pre, Surface Tension, Tensile Strength, Tin Concentration, Total Acid Number, Total Base Number, Total Water Content, Ultra Violete Absorbance, Upper Dust Explosion Limit, Upper Explosive Limit, Upper Flamability Limit, Vapor Density, Vapor Pressure, Viscosity, Viscosity Index, Volatile Organic Compounds (VOC), Volatility, and Water of Saturation.

A description of the interactive screen displays of the preferred embodiment of this invention appears at the end of the detailed description of this specification.

Authoring module 100 further comprises a deblending analyzer 115 and a substance processor 120 to produce hazard information of blends, materials derived from the original material being considered such as decomposition products, and hazard information for materials that are related to another material being analyzed. As the material data is entered, the system populates data tables in the database 500. All material data is linked by the material ID, an internal sequence number for each material. Components, decomposition products and classes are stored as materials and have a unique material ID. All hazard data, developed in the data association process 125, is linked to a material ID. Each hazard document is linked to a material. This data structure supports the generation of multiple documents from a single material. Additionally, changes to a material that is an ingredient can automatically be cascaded throughout the database using material ID. The system enforces referential integrity to ensure that every material ID is valid.

Entry of data into the data fields applicable to blends and decomposition products, as will most often be the case, initiates deblending processing 115 and substance processing 120. These processes are linked to a command to execute routines to perform the deblending and substance processing algorithms.

In the steps of deblending processing 115 and substance processing 120 decompiled hazard information is created. Decompiled hazard information is hazard information about a material, hazard information about the components of the material, hazard information about materials derived from the original material being considered (e.g., decomposition products), and hazard information for materials that are related to the material for which the material record is being created. Each component and decomposition product of a material is also a material in the database 500 and is associated with a unique material ID.

The deblend analyzer 115 populates a data table with the list of base level ingredients. To deblend each component, the processor pulls forward the base level ingredients of the component. It then aggregates these base-level materials with the base-level materials of the remaining components. The "purpose deblend" separates components by purpose before the aggregation step.

Where, for example, substance A is a mixture of substances B, C, and D and substance D is a mixture of substances E & F, deblending processing is the deconstruction of the mixture components. In subsequent steps this will be used to determine whether the substance as a whole is likely to be toxic based upon the status of its components and sub-components and their interrelationship. If the user indicates that deblending is necessary, the user is queried to provide the type of analysis. In the preferred embodiment of the invention, analysis types are summary deblend (analysis of the batch formulation of the material), total deblend (a complete analysis of all mixture components) or a purpose deblend (an analysis based on a predetermined category of mixture components such as "impurity" or "raw material"). Intermediate mixtures of materials are assigned a designator such as "SI" (system ingredient). A separate record is created for each such intermediate mixture and tagged for association with the final mixture. The intermediate mixture material records are used in the purpose deblend and total deblend analysis. In one embodiment of this invention, this process is conducted by a computer programmed routine for running MacKay Level 1 equations. These equations are used to model the distribution of a chemical in a hypothetical "unit world." This approach assumes that the chemical has no reactivity (i.e., it does not react, degrade, etc.) and that the "unit world" is at equilibrium.

This method accounts for the differential treatment of a material depending upon its quantity in the blend and its purpose as a component (e.g., the presence of some toxic materials only as an impurity may not render the mixture "toxic" according to certain regulatory schemes). The material records and SI records are ultimately processed through rule engine processing 155 with additional rules applied to account for the type of blend being considered. The resulting total deblend and purpose deblend compositions drive analysis and processing for association of the data with regulatory information to produce hazard information.

Substance processing 120 occurs via inter-linked computer programming routines comprised of a number of coprocesses. Substance processing 120 uses the results of the deblend analysis 115 to preprocess hazard information prior to data association 125. The result of substance processing 120 is the population of data tables associated with links to certain hazard characterization that is further associated with hazard information and judgments about such association in data association step 125. Additionally, output from exemplary substance process subprocesses 121, 122, and 123 independently populates data tables with a link to material records so that in some cases they may be pulled forward for document generation and dissemination.

Upon completion of deblend processing 115, the user is guided through a series of queries in regulatory applicable components subprocessing (RAC) 121 to determine whether the material or its components are subject to various regulatory categories such as state regulations, inventory reporting requirements, environmental regulations, and toxic substance control reporting requirements. An example illustrates the RAC subprocess. In this example, data are stored for two materials: a single component material such as benzene, and a mixture such as gasoline which contains benzene. For a single substance material, there are no components and so no component records would be created. A material regulations element data table in relational database 500 would be populated but another data table for components (a component regulations element table) would be blank. For a mixture such as gasoline, there may be regulations which specifically list the mixture as a regulated material. More commonly, the mixture may be regulated because it contains a regulated component such as benzene. RAC processing 121 makes this distinction and populates a data table for components if necessary. Thus, the data table associated with material regulations would be populated for both single substance (benzene) and mixture (gasoline) but the component data rows would be populated only for the mixture (gasoline) using the record previously stored for benzene.

RAC processing 121 functions by comparing the components relating to a material record to a data list of regulated components. If the component of the material being considered appears on such a list, RAC processing associates the material with the regulated component. This association is linked to a command which causes a data table of regulated components to be populated. This data table is further compared to a data table of values of component concentrations which, if present, must be reported. This is done via reportable quantity/threshold planning quantity (RQ/TPQ) subprocessing 121a. This subprocessing routine calculates the quantity of a component that must be spilled, released, present, or associated with some type of incident in order for an event to be reportable to regulatory agencies. If the component in the component data table contains greater than the threshold quantity of the given material or component in question in subprocessing 121a then a further association is made and an additional data table is populated. Ultimately, this data table will be used in document generation.

In marine pollutant component subprocessing 122, each component element identified above is subjected to further analysis to determine the degree to which it may be characterized as a marine pollutant. A data table in relational database 500 is populated with lists of materials which are characterized as marine pollutants according to regulatory schema or available testing data. For each component, there may be zero, one, or more than one marine pollutant component (MP Component). Using the summary composition, the processor calculates the marine pollutant (MP %) and priority pollutant (PP %) percentage contribution of each component to the overall material. In the preferred embodiment, these data are associated with tags to indicate whether a given pollutant is a priority pollutant. If the component is a priority pollutant then a concentration of one or more weight percent of the component causes the material record for the material comprised of the component to be linked to a data table of marine pollutants. If the component comprises 10 weight percent or more of a pollutant which is not a priority pollutant the same result is caused to occur.

In employee protection preprocessing 123 exposure limits are initially defined for a particular material record. This exposure limit is then "pulled forward" when the original material appears in the total deblend composition of another material record via a link between the two.

This employee protection preprocess occurs as follows. Each row in the composition data table generated during deblending is annotated with code that associates an indicator that a material or its components or decomposition products has been regulated. This occurs when the material is linked to another material record and that material is directly regulated. The relevant exposure limits are determined for a material by examining the total deblend composition and retrieving the limits for those materials (i.e., limits with the same short name as the total deblend composition rows).

In order to generate the proper relationship code for each limit, the application determines whether a row has been selected as a result of component relationship or if the limit was defined for the active material. Based on this calculation the application inserts the corresponding code in a relation column of a data table for the preprocessor. If the active material is equal to the exposure limit in the selected row of the preprocessor data table this means that the exposure limit was defined for the active material. In this case the limit row is marked with a relation code of "MA". If the active material is not equal to the exposure this means that the exposure limit was defined for a component material. In this case the limit row is marked with a relation code of "CO". The preprocessor copies the base values (both % weight and % volume) for the maximum concentration from the each row in the total deblend composition to hidden columns in a datatable to be subsequently used during employee protection recommendation process 126.

Each of the preprocessing and coprocessing steps above also contain programming code that will analyze decomposition products in an analogous fashion. For example, relevant exposure limits based on the decomposition products that have been defined for the active material are identified. The preprocessor then examines the decomposition products assignments made for the material in the data table for decomposition products. It then identifies any cases where a decomposition product has been related to a material record. If links to material record(s) exist, the processor retrieves exposure limits by comparing the short names from the reference table to the short names in the data table for exposure limits. If any of the names match, the relevant exposure limit is pulled forward in the same way the component data is pulled forward.

In substance processing 120 relationships can also be defined to account for the interaction of the ingredients of the blend. For example, Material A may decompose into components B and C after storage at 22° C. for more than one year. Known relationships between final decomposition product concentrations and physical properties of the resulting mixture (e.g., boiling point elevations attributable to a dilute solution of solute B in solvent C) can be used to determine the physical properties and related hazard information after a period of time under a given set of conditions.

Alternatively, such relationships can be defined according to models which will predict the decomposition products and their concentrations based upon predicted conditions such as time and temperature. For example, a library of chemical reactions can be constructed. Depending upon the desired degree of sophistication of the models, one can associate kinetic, thermodynamic, catalytic, and other data to the chemical reactions stored in the library. A library of modeling routines can then be compiled which relate the chemical reaction library to decomposition products and their concentrations; blend components and their concentrations; type, size, and composition of storage or transport vessels, expected temperature and physical conditions, and time of storage. The modeling routines could then be run to determine the most likely composition of a material stored or shipped under the conditions indicated.

Thus, upon completion of substance processing 120 data tables are populated which relate material components and decomposition products with regulatory status, reportable quantity data, pollutant characterization, and employee protection requirements.

The aforementioned processes in which material records are created for each material, component, decomposition product, and related material is referred to herein as data decompilation.

In data association step 125 the system user is guided through an inquiry process in which all of the data elements of a material record organized by the material entry step 110, deblend process 115, and substance process steps 120 are subjected to a process of regulatory pre-evaluation. That is, the program directs the system user through a series of judgments required by regulations relating to hazard information. At the completion of the aforementioned process in which each data element which has been decompiled and is then subjected to a data association process, all of the data of all material records relating to a material, its components, decomposition products, and related materials is associated with hazard communication data. Upon association of the material records with the data produced in the data association process 125, each such association is assigned a data code.

The material records are then processed in the rule running process 155. The rule engine which performs the rule running process is a set of predetermined or programmed rules which are applied to the material records so that standard phrases are associated with the substance in the communication produced by the system (e.g., MSDS sheet or product label). A sequence of computer programming instructions assign standard phrases to the material records. This associates the outcome of each application of a rule criteria to each material record and the time at which the rule was last run. If the rule criteria or material record is changed, the process can be rerun to ensure that the assignment of the outcome of the application of the rule and the standard phrase pertaining to that outcome are current. Processing material records through the rule engine creates consistency in the content of hazard documents and labels that has not previously been attainable.

The rule engine shown processing associated data in 155 is preferably an open system in which rules may be defined by the user. In the most preferred embodiment of this invention, the rule engine ascribes the following types of attributes to the material record to which it is applied: material description, composition, physical and chemical properties, regulations, transportation classifications and requirements, toxicology regulations, environmental toxicology regulations, employee protection measures, and labeling information.

Rules are comprised of one or more rule criteria statements. Rule criteria statements are logical boolean statements (preferably, true or false). Complex criteria can be created from combinations and relationships among individual rule criteria statements using logical operators such as "AND", "OR", "NAND" and "NOR" statements. For example, the user may wish to prescribe the following rule: If the material is regulated by the Department of Transportation and has a primary class/division of 3C(Combustible Liquid) and is not a Marine Pollutant and the material does not contain a DOT Hazardous Substance or the smallest reportable quantity for a Hazardous Substance is greater than or equal to the weight of 119 gallons, then print the standard phrase "This material is not regulated under 49 CFR if transported in a container of 119 gallon capacity or less" in the Transportation section of the Material Safety Data Sheet and the Transportation Advice Card. Rules can also be created based upon mathematical scaling, curve fitting, and/or modeling using, for example, the methods set out in U.S. Pat. No. 5,724,255 (Portable Emergency Action System for Chemical Releases) which is incorporated herein by reference.

The system may be used in different countries or by people who speak different languages. It is a nontrivial matter that the rule engine processing 155 accurately produce the message intended by the construction of the rules. This can be accomplished in a variety of ways. The rule engine can be constructed so that the output of each rule application is provided in the target language in which the system will be applied. This approach is preferred when the hazard communication regulations change in a particular country. Alternatively, a separate translator may be combined with the rule engine so that the output of rule engine processing 155 is subsequently treated to translation in one or more languages different from that of the rule engine itself. For example, a Spanish language MSDS for US-based workers will use the same OSHA rules as those used to prepare the English language MSDS and will apply translations after running the REP.

The rule engine comprises a series of computer programmed routines in which the data codes or underlying hazard data are compared to one or more boolean expressions to determine whether they satisfy a given condition. The routines are drawn from user defined rules 160. Each data code or underlying hazard data is substituted for one or more variables used to form the logic of the expression. Satisfaction of the condition against which the data code or data is being evaluated causes a link between the material record and a hazard communication phrase in a database of phrases, the phrase library 165. For example, after conducting the data association process 125, it may be determined that a material component has an $LD_{50}$ at 50 ppm for lethality by inhalation and that breathing apparatus are required when working the material component. This may be assigned a data code, X to categorize its $LD_{50}$ value and a data code Y to represent employee protection measures required. A value Z may be assigned to represent the quantity of material kept on hand. This data is then subjected to rules from user assigned rules database 160 which reads: "If $LD_{50}$>X and Y and Inventory on hand>Z then 'Material is highly toxic, breathing apparatus required'".

Once a material record is assigned a phrase by rule running process 155, the system user finalizes the hazard information in step 170 by viewing the association of the phrases with documents such as MSDSs contained in document template database 175. The association is completed by acceptance of the final form of the documents for a given material in document generation process 180 subsequent storage to the documents in document database 190.

In document generation process 180 documents are prepared based upon pre-formatted templates or user defined documents. In either case, a document form is first defined by linking document objects. A document object is a block of information and/or logical expressions including text or graphics that pertains to a document. It is comprised of one or more expressions that combine data items with logical operators, functions, and constants to produce a single value or a table of values. Document objects can be singular or tabular, graphics or text and can produce lists of items. Document objects include logic to compute new data values from data items in the database. For example, one can define an object joining a table of values associated with a material with the short names for each of the materials and their components to which they are associated. One can then join this object to a unit of measure table to provide descriptions for each concentration unit of measure code. A logical expression can be joined to this table object to screen for only those objects having more or less than a particular threshold concentration value. This could be used, for example, to check for benzene concentrations above a certain level and populate MSDS sections requiring this information.

Document forms can be modified by changing particular document objects. Thus, when a regulation changes, one can modify the document object which affects the computation or communication driven by the regulation. Each individual document and table need not be affected. For example, if the regulations upon which the document object described above required reporting a lower threshold concentration value for benzene, one need only modify the document object containing the logical expression for screening concentrations. The underlying data tables and other related document objects need not be affected at all. This process is facilitated by document registration. This is the process in which the document form, comprising document objects and references or tags pointing to them, is saved to a database in the authoring module. The authoring module then creates an identification of every document form, document object, and every document tag. The user need only access the document register to identify the object to be modified and then modify it.

The documents produced in this process can be printed or prepared as output from the document generation process (e.g., printed on hard copy and manually distributed) or it can be distributed via distribution module 200 as described below.

The document generation process is preferably conducted using native SQL applied to relational database 500.

The aforementioned processes in which phrases associated with a material record are formed into a final document is referred to herein as recompilation.

Figure 3:
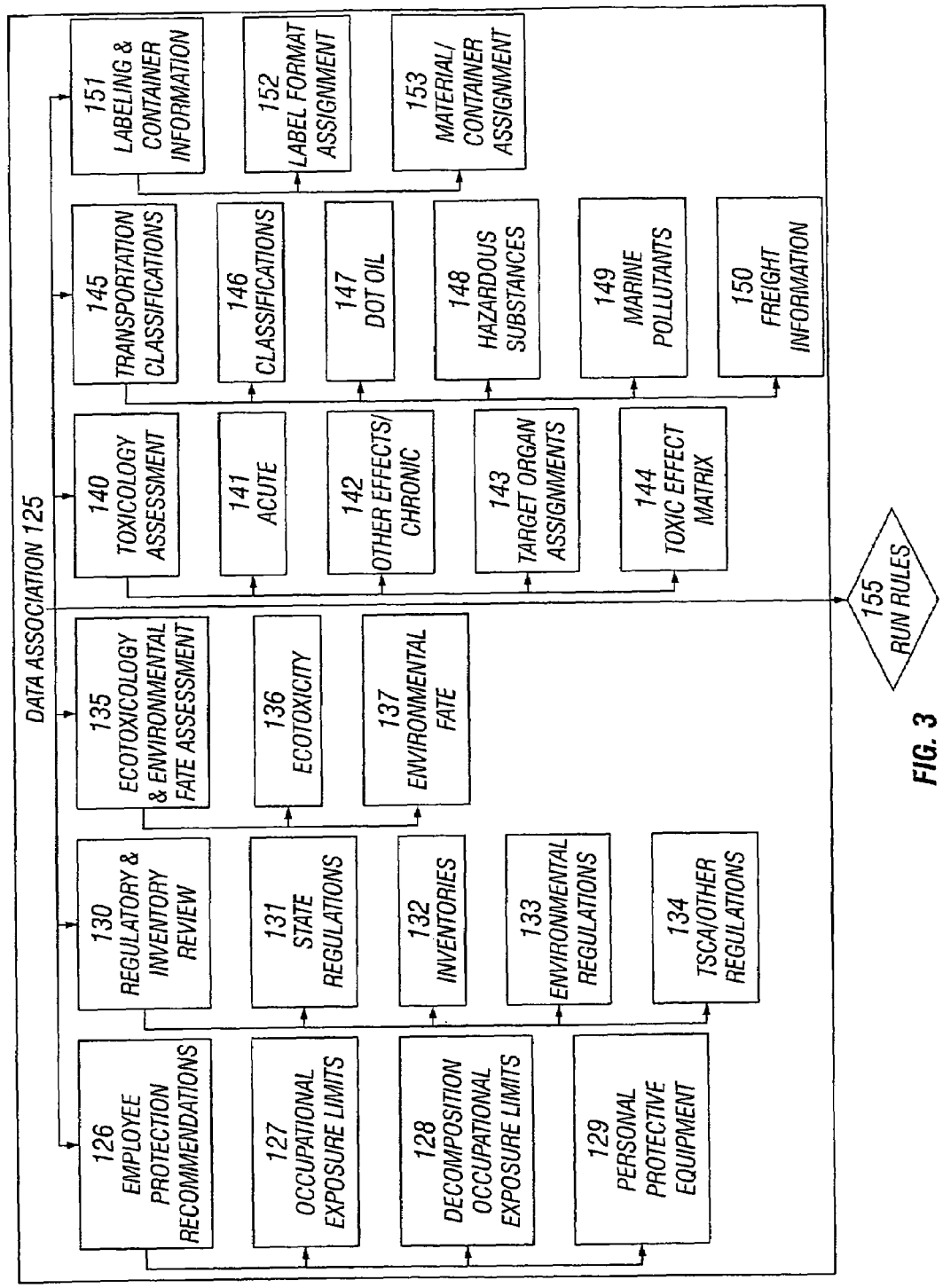
FIG. 3 is a schematic view of a data association process performed within the authoring module (process) of this invention.

FIG. 3 illustrates the data association process 125 in the detail necessary to more fully understand the invention and the example. In each process and subprocess of the data association process 125 the system user is guided through a process in which each data element of a material record is considered against well accepted formulae and evaluations required by different regulations relating to hazard communications. The system is programmed to conduct these inquiries based upon existing regulations such as Australian Inventory of Chemical Substances, California Prop 65, California State Hazardous Substances List, California State Right-to-Know, China Inventory, China Product Registration, Clean Air Act, Clean Water Act, Comprehensive Environmental Response, Compensation and Liability Act, Connecticut State Right-to-Know, Connecticut Toxic Substances List, Department of General Medicine, Direct Food Substances Affirmed as Generally Recognized as Safe (Subpart B), Domestic Substances List, Emergency Planning and Community Right-To-Know Act, European Inventory of Existing Commercial Chemical Sales, Florida Right-to-Know Hazardous Substances, Florida Substances List, Florida Toxic Substances Right-to-Know Reporting, Food Additives Permitted For Direct Addition to Food for Human Consumption (Subparts B–I), Food Additives Permitted in Food: Interim Basis or Pending Additional Study (Subpart B), German Inventory, Hazardous Substances and New Organisms Bill (?), Hazardous Substances regulated by DOT due to CERCLA listing by EPA, Illinois Toxic Substances Disclosure to Employees Act, Indirect Food Additives: Adhesives and Components of Coatings (Subparts B–C), Indirect Food Additives: Adjuvants, Production aids, and Sanitizers (Subparts B–D), Indirect Food Additives: General (no subparts), Indirect Food Additives: Paper and Paperboard Components (Subpart B), Indirect Food Substances Affirmed as Generally Recognized as Safe (Subpart B), Indirect Food: Polymers (Subparts B–C), Industrial Chemicals Act, Irradiation in the Production, Processing and Handling of Food, Japanese Chemical Substances, Korea Inventory List, Korea Registered List, Louisiana Right-to-Know Reporting List, Maine Right-to-Know List, Massachusetts CONEG, Massachusetts Right-to-Know Substance List, Michigan Critical Materials List, Minnesota Right-to-Know List, New Jersey Right-to-Know Substances, New York Acutely Hazardous Substances, New York Release Reporting Substances, Non-Domestic Substances List, Pennsylvania Right-to-Know Hazardous Substances, Philippine Inventory of Chemicals and Chemical Substances, Prior-Sanctioned Food Ingredients (Subpart B), Resource Conservation and Recovery Act, Rhode Island Hazardous Substances Right-to-Know Act, Rhode Island Right-to-Know Act Hazardous Substances, Safe Drinking Water Act, Secondary Direct Food Additives Permitted in Food for Human Consumption, Substances Generally Recognized as Safe (Subparts A–I), Substances Prohibited From Use in Human Food (Subparts B–C), Superfund Amendments and Reauthorization Act—Section 302, Superfund Amendments and Reauthorization Act—Section 313, Superfund Amendments and Reauthorization Act—Sections 311/312, Swiss Listing of toxic Substances for Manufacturing and Marketing, Test: California Process Safety Management, Thailand Inventory, Toxic Substance Control Act, Toxic Substance Control Act Inventory List, Toxic Substances Control Act, Transitional Chemicals, and United States Department of Agriculture.

In data association process 125, the presence or absence of particular parameters of a material record triggers the application of a rule to that record which then requires the user to interact to conduct the analysis through an interactive computer display screen. These processes permit the approximation or evaluation of a material, one or more of its components, its decomposition products, or a related material based upon the data from the original material record. For example, where no environmental fate data is available for a mixture containing components A and B, the application of well accepted formulae incorporated into environmental regulations will be applied to A and B to populate a material record for the environmental fate of the mixture itself. The system user can also apply judgment to the process to ensure that irrational results are not obtained. For example, if a mixture contains a highly toxic component at a very low concentration, the user can determine whether such a low concentration negates the toxic characteristics of the component. The user can then cause (via direct input) the material record to reflect this judgment for the mixture as it is prepared, used, stored, and/or transported.

The system queries the system user about information necessary to make employee protection judgments in employee protection processing step 126. This is done through three subprocesses. The occupational exposure limits subprocess 127 and the decomposition occupational exposure limits subprocess 128 use the results of substance processing 120 to identify regulated exposure limits for the material, its components and its decomposition products. For example, in a mixture of component A and B, component B may have a short term exposure limit of 10 ppm as defined by OSHA. Subprocess 128 would be triggered by the output of substance processesing 120 and deblend processing 115 indicating the mixture contains greater than 10 ppm of component B. Subprocess 128 would then query the user to apply judgment to determine whether the form in which the mixture is produced and stored requires that the mixture be considered to fall within the short term exposure limit. The user can then accept or change the proposed association the short term exposure limit with the material record for the mixture. Subprocess 128 would perform a similar process based on the decomposition products of mixture A or component B. In personal protection subprocess 129, well accepted formulae incorporated into or required by regulations are applied to the data to determine whether particular employee protective measures are required for handling any material with which a material record is associated such as a mixture, its components, siblings of those components, decomposition products of the material and its components, or other related materials. For example, the system may indicate to the user that material X contains 10 ppm Y and that regulations require a warning that glove protection is required when handling more than 100 ppm Y. The system user will be queried to provide information that can be used to make a judgment about whether the concentration of Y may necessitates the attachment of that warning on labels and documents concerning material X. This could include questions about the storage conditions of material X since this (combined with existing information about volatility) can affect concentration of products Y and Z. The system user may also be advised of recommendations proposed by the system for the use of protective equipment such as goggles, gloves, respirators, and safety suits. Such recommendations are generated links to the combined output of subprocesses 127, 128, and 129.

In regulatory and inventory review process 130 the user is guided through the state regulations 131, inventories 132, environmental regulations 133 and TSCA/Other regulations 134, subprocesses to determine whether each material, component, and decomposition product are listed in corresponding governmental regulations or are regulated. The regulatory applicable components subprocess (RAC) 121 identifies regulated materials and calculates reportable quantities. For state regulations subprocess 131, the RAC processor automatically determines the applicable regulations using the total deblend composition. The user cannot change these results. For example, the system will list the different state regulations that include a component such as benzene. In the inventories subprocess 132 and TSCA subprocess 134, the RAC process pulls forward the inventory status of components using the summary composition but does not associate any data with the material. The user is expected to review this information and determine the inventory status of the material. For example, the user can view the inventory status of benzene and other components to determine whether the mixture is already covered on the inventory list. In the environmental regulations subprocess 133, all component regulations are determined automatically by the RAC process based on the total deblend composition. However, the user must manually select which of these records apply to the material. During the regulatory and inventory review process 130 these results are marked with the material record as "reviewed" and "regulated" or "not regulated". For example, the user can indicate the mixture is regulated by states but is not regulated under the TSCA.

In ecotoxicology and environmental fate assessment process 135 the system user is guided through ecotoxicity subprocess 136 to determine whether the material, its composition, or its decomposition products cause environmental effects to plants and aquatic life based upon known characteristics and material testing. Test results are entered into the system by a valid exposure and sub-class combination or they are pulled forward from the component records to the material. The environmental fate subprocess 137 which operates in a similar manner to the ecotoxicity subprocess 136, determines the ultimate impact on the environment should the material, its components, or decomposition products be released. The system determines the environmental hazard effects, such as aquatic toxicity, by comparing test data (e.g., Lethal Concentration studies for 50% of a population of fish) or data for related materials with rules prescribed by the appropriate regulations. The data is entered through the system screens and stored in the database 500.

The system user is also guided through toxicology assessment process 140 to associate human health effects of materials with the material record. This is done through the acute effects subprocess 141 in which well accepted formulae incorporated into or required by regulations are applied to the data to determine the severity and type of effects that are expected upon contact with any material with which all of the material records are associated with the data are found. For an acute effect such as oral lethality, the system user enters test results data that show the concentrations required to kill 50% of population of mammals such as rats. If no test data is available for the material, the system user typically selects data on the component with the lowest concentration. The logic of the subprocess associates the data with the reporting requirements for the material and all related material records. Additionally, the chronic effects subprocess 142 applies well accepted formulae incorporated into or required by regulations to the data to determine whether long term effects are expected with all of the material records associated with the data. For example, studies for both components of a mixture may identify long term carginogenic effects of the mixture itself. The chronic effects in particular target organs relating to materials and their components are associated with material records in subprocess 143. In the toxic effect matrix subprocess 144, the system user identifies the studies and chronic results to attribute to the material. Through the data association conducted in this subprocess, a toxic effect summary statement is constructed and associated with the material records.

In transportation classification process 145 similar processes to those already described are applied to classify the materials, their components, siblings of those components, decomposition products, and related material for shipping and transportation warning documentation. In classification subprocess 146 the domestic and international classification schemes are applied against material records to associate labeling instructions and shipping papers such as designation as a "hazardous substance", assignment of a shipping number on truck markers and the like. For example, the user can classify the material as "hazardous-flammable" for land transportation and as "restricted" for international air transport. In DOT oil subprocess 147 material records are evaluated to determine whether mixture is to be considered an oil and how it is to be treated (e.g., precautionary measures required for water transportation). The components and mixture are evaluated to determine the existence of DOT hazardous substances in subprocess 148. The RAC 121 preprocesses this information. In marine pollutant subprocess 149 material records are associated with evaluations to determine whether any material associated with the record or any particular amount of a mixture containing such a material would be characterized as a marine pollutant. The system user can calculate the marine pollutant and priority pollutant percentage using marine pollutant comoponent subprocessing 122. For example, if 10% of a material is considered a marine pollutant, then the user can mark the material record associated with the material as a marine pollutant. This marker stays associated with the material record for subsequent use in rule processing. The user can also enter the results of test data. The freight information subprocess 150 identifies the freight mode and class required or desired for each trade name of the material. This information can be used to calculate shipping fees.

In labeling and container assessment process 151 the system user supplies the system with information about the container and shipping methods which are expected to be used with a material and how much material will be present in those containers. The label format assignment subprocess 152 stores user entered data on the specific types of labels for the material. Label formats will vary based on container (e.g., drum) and agency (e.g. DOT). Data is entered in this part of the process through material container assignment subprocess 153, again preferably through interactive computer display screens. These data records are then associated with regulatory instructions for the treatment of the materials in containers of the type to be used and information for labeling those containers. For example, the standard fill amount of a specific container is used to determine whether the container contains a reportable quantity of a regulated chemical. If component A of a mixture must be reported to a government agency if 100 gallons or more of the mixture is spilled, then a 55 gallon drum would not include this reportable quantity while a rail car load would. This container assignment subprocess 153 completes the data association process 125 of the preferred embodiment of this invention.

Figure 4:
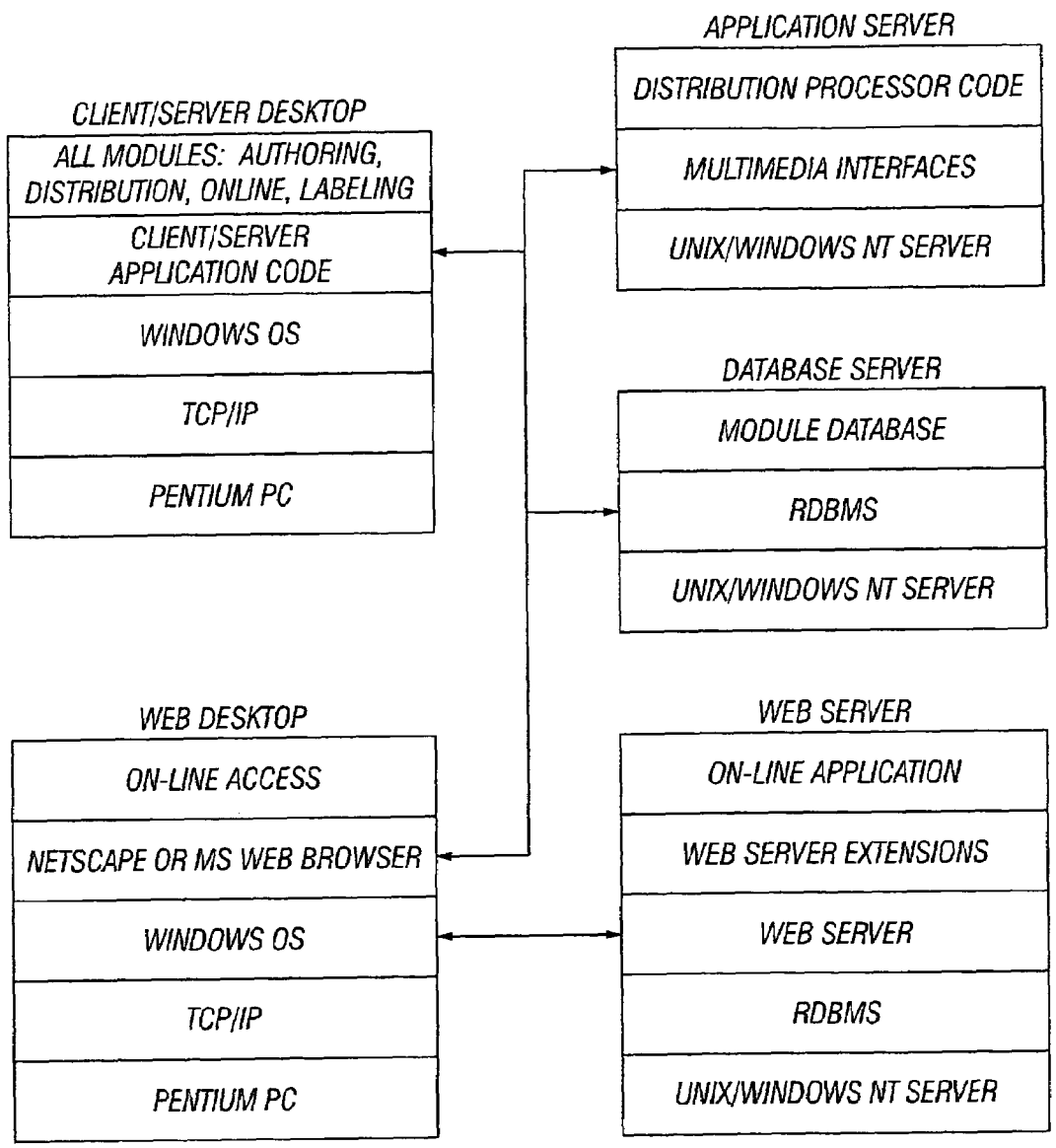
FIG. 4 is a schematic view of a technical architecture useful in the practice of this invention.

In the preferred embodiment of this invention, the system is programmed to operate in a cooperative processing environment using a combination of client/server and web system architectures. FIG. 4 shows the preferred technical architecture of the system. Users access the system through application software on a desktop computer (all modules) and through a web browser for the online module 300. In both cases, the client workstation supports the Windows operating system (3.x, 95, 98, NT) and runs the TCP/IP networking protocol and Intel-based personal computers. In the client/server architecture, screens for user interaction and selected logic processing runs on the client desktop.

All data is stored in the database server, a dedicated workstation running relational database management system RDBMS software and the UNIX or Windows NT operating system. The system will run with lead RDBMS products such as Oracle databases, Microsoft SQL Server and Sybase SQL Server. Each module has its own database.

The system also includes an application server, preferably running in Windows NT, to operate the distribution module 200 and to support other computational processing such as rules and document generation. This server runs specific application code.

The final element is the web server to support employee access to the online module 300. The web server provides general access across heterogeneous computing environments and minimizes software deployments to desktops. The server preferably runs under UNIX or Windows NT, includes a RDBMS or links to a database server, runs web server software such as Microsoft's Internet Information Server, and includes the web applications and appropriate extensions for the web server.

The interactive screen displays of the preferred embodiment of this invention include:

Material Search Screen. Allows users to search the database for a particular material record. Interface for adding, editing, and deleting system materials.

Composition Search Screen. Used to enter compositional information on which to search for matches or like materials. Used to facilitate data entry of material composition information.

Delete Processor Screen. Removes a material record from the database.

Copy Processor Screen. Creates a new material record based on the values from a related material record. The system user may chose such a material that is related based upon user judgment or programmed logic which searches other material records for similarities to the attributes or properties of a material for which information is sought.

Revision Processor Screen. Communicates a command to create a revised record for a material record which has been completed (i.e. a final record) or is no longer produced, stored, sold, or transported.

Material Information Screen. Used to enter general descriptive information about a material, and to associate a material to a data group and, if appropriate, to a material class.

Composition Screen. Used to enter the components that make up a material, including the concentration of each component, its purpose in the material, and the information that should print for the component on hazard documents.

Composition Comment Pop-up Screen. Used to enter or view comments related to specific composition types.

Copy Compositions Screen. Allows users to construct a composition based on parts from other composition types. All or part of a composition may be copied to a different material record. For example, a user may copy all or some information about benzene into a material record for gasoline by instructing the system to do so.

Component Print Information Screen. Used to enter print information for component rows in the Purpose Deblend composition type.

Trade Names Screen. Interface used to enter trade name information about a material. Each material record has one "product" trade name that is used on documents to identify the material. This name is associated with a company and is assigned to a document group number. When a material is rebranded, "rebrand" trade names can be defined. Each rebrand trade name is also related to a defined company and document group number.

Product Code Assignment Screen. Interface for assigning product codes to the trade name after it is defined on the Trade Names Screen. These assignments determine the product codes that print on documents generated for that material and company header. The company associated with the trade name differentiates product codes, meaning that the same code can be assigned to more than one company for the same material.

Product Use Assignment Screen. Used to enter data to associate a trade name to relevant product uses.

Trade Name Information Screen. Used to enter business classification values for a trade name, such as API and RFG codes.

Synonyms Screen. Used to enter data to define alternate naming information for a material.

Physical/Chemical Properties (Record View) Screen. This screen is the primary means used to enter and view property data associated with a material.

Bibliographic References Screen. Allows the user to associate bibliographic reference information and a reference date to a property record.

Decomposition Products Screen. Used to input data and judgments about data used to make decisions on the decomposition hazards associated with a product based on information stored about its summary components. Permits the user to view the decomposition products data stored for the summary level components. Based on professional judgment, the user can associate any or all of these hazards to the material, or add new hazards.

Hazard Summary Questions Screen. Allows the user to enter and view responses to Yes/No questions which provide characteristic information about materials, and store comments specific to each question describing how the determination was made for that material.

Summary Screen. Provides a summary of the material's regulatory status for each of the four areas in the Regulations topic area: State Regulations, Inventories, Environmental Regulations, and TSCA. The user designates whether each subject area is applicable to the material.

State Regulations Screen. Allows users to identify component materials that are subject to state regulations and enter state regulatory data applicable to the active material.

Additional Regulatory Data Screen. Used to enter and store additional regulatory information associated with a specific material and specific regulation in the State Regulations, Inventories, Environmental Regulations, and TSCA subprocesses.

Inventories Screen. Allows users to identify materials that must be inventoried and reported to regulatory agencies. Applicability of a material is based on two conditions: 1) whether the material itself is subject to inventory regulations; or 2) whether the material contains component(s) that are subject to inventory regulations.

Environmental Regulations Screen. Allows users to identify materials that are subject to environmental regulations. Applicability of a material is based on two conditions: 1) whether the material itself is listed in the regulations; or 2) whether the material contains a component that is subject to the regulations.

TSCA Screen. Allows users to identify materials that are subject to the non-inventory portions of the Toxic Substances Control Act (TSCA) regulations. Applicability of a material is based on two conditions: 1) whether the material itself is listed in the TSCA regulations; or 2) whether the material contains a component that is regulated by TSCA.

Classification Screen. Allows users to specify the regulatory status of a material and classify the material according to DOT and other regulatory agency classification protocols.

DOT Oil Screen. Used to enter information to determine whether the material is classified as an oil under DOT regulations. Determination is made using the quantity of oil in each of the summary components of a material.

Hazardous Substances Screen. A modified version of the Environmental Regulations Tab, which is used to store similar data on regulatory applicability of hazardous substances, primarily from DOT regulations. The regulatory applicability of a material in this tab is based on two conditions: 1) whether the material itself is subject to the regulations, and/or 2) whether the material contains a component that is subject to the regulations.

Hazardous Substances Additional Data Screen. Enables entry of additional regulatory information associated with a specific material and specific regulation.

Marine Pollutants Screen. Used to enter data to determine whether a material qualifies as a marine pollutant based on the marine pollutant classifications of its components.

Freight Information Screen. Used to enter data to identify freight information for each product trade name within a material. Information provided includes identification of the freight shipping modes (e.g., tank car, tank truck) and the hazardous goods classification code, if applicable.

Material OEL (Occupational Exposure Limit) Screen. Used to view the exposure limits for a material. The screen displays the selected limits by qualifier, country, and filter concentration.

Decomposition OEL Screen. Used to view OELs assigned to the material because of its decomposition products.

Personal Protection/Exposure Control Screen. Used to enter information about the required safety equipment (such as special devices or clothing) and engineering control recommendations for handling a material.

Exposure Limit Data Screen. Used to collect the detailed information about every agency exposure limit for a material. Allows users to enter multiple test rows for each record.

Biological Exposure Indices Data Screen. Some agencies or organizations, such as the American Conference of Governmental Industrial Hygienists (ACGIH), use biological monitoring measures to augment their standards. Biological Exposure Indices, entered for the active Exposure Limit using this Screen, are the reference values used to represent the levels of determinants which are most likely to be observed in specimens collected from a healthy worker who has been exposed to chemicals.

Review Screen. Allows users to enter and view the overall comments about a substance's human health hazards. In addition, the screen lists the relevant references that have been associated to the active material. Included in the listing are any sibling, class, or component references that have been copied forward and selected as the authoritative row on the Acute screen, or related to a test that was used as the basis for writing a toxic effect summary on the Toxic Effect Matrix Screen.

Acute Screen. Used to build a list of relevant acute health effects testing data for the active material. Tests are entered by selecting a valid end point and route combination and adding a row to the test listing. The listing may consist solely of test data on the material itself. In addition, tests from class, sibling, or component records can be pulled forward to the active material using the Copy button. A hazard code that is used by rules processing to select standard phrases can be entered for each test row.

Other Effects Screen. Used for entering chronic or sub-chronic effects test data for the active material. Tests are entered on this screen by end point, route, and reference identification number, to accommodate studies with multiple end point testing for chronic and sub-chronic effects.

Target Organ Assignment Screen. Used to associate target organ effects to a chronic or sub-chronic test entered on the Other Effects Screen. Summary statements that are ultimately used on the Toxic Effect Matrix Screen to create Toxic Effect Summaries are also entered in this screen.

Toxic Effect Matrix Screen. Used to compose Toxic Effect Statements for hazard documents. These statements are produced based on the other effects testing data related to the active material. Each toxic effect can be mapped to an other effect end point, a particular target organ, or neither. This mapping is created using a behind-the-scenes assignment reference table (via relational database 500). The relationship is used to determine what other effects data (from the material, class, siblings, and components) needs to be available while constructing the toxic effect statement used on hazard documents.

Review Screen. Allows users to enter and view the overall comments about a substance's environmental hazards. In addition, the screen lists all the "relevant" references that have been associated to the active material. Included in the listing are any sibling, class, or component references that have been copied forward and selected as an authoritative row on the Eco-Tox or Eco-Fate Screens.

Eco-Tox Screen. Used to enter data to build a list of relevant environmental effects testing data for the active material. Tests are entered by selecting a valid exposure and sub-class combination and adding a row to the test listing. The listing may consist solely of test data on the material itself. In addition, tests from class, sibling, or component records can be pulled forward to the active material using the Copy button.

Eco-Fate Screen. Used to enter data to build a list of relevant environmental fate effects testing data for the active material. Tests are entered by selecting a valid media and sub-class combination and adding a row to the test listing. The listing may consist solely of test data on the material itself. In addition, tests from class, sibling, or component records can be pulled forward to the active material using a Copy button.

Label Format Assignment Screen. Used to assign a label format to each document type. Assignments are specific to a document group, regulatory agency, and language combination. The list of document types for which format assignments are needed is determined from the Material-Container Assignment Screen.

Site Assignment Screen. Allows users to specify the labeling sites that are authorized to print labels for a particular combination of document group (which is a combination of document group number, trade name, and company name), agency, and language, and document type.

Run Rules Screen. Used to specify the rules to be evaluated for a material and to initiate rule processing for a material.

Material-Standard Phrase Assignment Screen. Used to review and modify standard phrase assignments generated by rules processing. Shows the standard phrases assigned within a standard phrase category and the rule used to make the assignment. Also shows which rules have been evaluated for the material, whether the rule was evaluated as true, false, or if there was an error in evaluating the rule. Accepts data entries to modify the assigned phrase.

Template Selection Screen. Allows the user to specify the documents to produce for the active material, by assigning registered document templates to document group numbers (trade name/company combinations). Once a template is assigned to a document group number, it is available for generation by the document generation process.

Revision Information Screen. Allows the user to assign a revision number, revision date, revision comment, and review date to any document group number/regulatory agency/document type combination. Revision information is applied to all documents generated after the revision information has been altered.

Options Screen. Allows the user to specify in detail the set of documents and options to be used in the document generation process. The user selects the type of generation to perform, the message log options to use, and the set of documents to generate.

Documents Screen. Provides the user with a list of generated documents. This list displays document group number, document name, revision, status, and auditing information for each document. The user may selectively regenerate, view, or approve single or multiple documents, and may delete any document in a Draft status.

Document Viewer Screen. Allows the user to review any generated document by using third-party controls such as High Edit, Netscape Navigator, and Internet Explorer to provide a WYSIWYG display of the generated document. The user may print or save a copy of the document to a local or network drive.

Specific Classifications Screen. Invoked in the Physical/Chemical Properties, Regulations, Human Health Effects, and Environmental Effects topic areas. The Specific Classifications Screen is used to enter or view the classification rankings for a material. The ranking schemes that are available on this Screen may be based on outside agency scales such as SARA, HMIS, and NFPA, or internal corporate schemes. Classifications are broken down into discrete categories ("qualifiers") that need to be scored. Classifications may have multiple qualifiers; for example, Fire and Acute are two qualifiers for the SARA classification and is each scored separately.

Bibliographic References: References Search Screen. Invoked in the Human Health Effects and Environmental Effects topic areas. Used to search for bibliographic references. Allows users to search for and select reference records to update. Also used to find references for a material and associate a status value to each one.

Bibliographic References: General References Data Screen. Invoked in the Human Health Effects and Environmental Effects topic areas. Used for entering data on a specific published or proprietary study. The data collected on the Screen is sufficient to obtain the study from a private provider or public information resource. In addition to collecting all the basic background data about references, this screen permits the association of the reference to a toxicologist reviewer.

Bibliographic References: Materials and End Points Screen. Invoked in the Human Health Effects and Environmental Effects topic areas. Used to associate chemicals tested to a reference and identify testing end points. Collects information that can be used to search for references in the future and also allows users to create links from a reference to one or more material records.

Bibliographic References: Abstract Screen. Invoked in the Human Health Effects and Environmental Effects topic areas. Used to enter an abstract for the active reference. The abstract is not related to any one of the reference materials but summarizes the results of the test for all chemicals tested. The abstract may be free text entered or cut and pasted from another electronic record.

Material-Standard Phrase Assignment Screen. Invoked in the process of running rules 155. Displays the standard phrases assigned within a standard phrase category and the rule used to make the assignment. Also shows the rules that have been evaluated for the material, whether the rule was evaluated as true, false, or if there was an error in evaluating the rule. Used to review and modify existing standard phrase assignments without having to re-run the rule process 155 itself.

Material-Container Assignment Screen. Invoked in the Transportation 145 and Labeling 151 processes. Allows the user to specify the allowable containers for material shipping. From this information, the system can determine the list of unique document types for which labeling formats are required in the Label Format Assignment Tab in the Labeling topic area.

We claim as our invention:

1. A data-centric hazard communication apparatus comprising:
   a) an authoring module for identification of hazardous material and its characteristics, the authoring module further comprising:

an automated means for selectively decompiling said hazardous material, determining its components and decomposition products and their respective characteristics;

an automated means for associating said hazardous material and said component characteristics with hazard information, using a user defined set of hazardous material rules;

and a means for recompiling said hazardous material and said components associated with hazard information to provide hazard information about the hazardous material, its components, decomposition products of said hazardous material, and substances related to said hazardous material; and b) a means for disseminating hazard information about said hazardous material, its components, decomposition products of the material, and substances related to the hazardous material wherein said means for disseminating hazard information communicates with said authoring module.

2. The apparatus of claim 1 wherein said means for decompiling said hazardous material comprises a deblending analyzer.

3. The apparatus of claim 2, wherein said means for decompiling hazardous material further comprises a substance processor.

4. The apparatus of claim 1 wherein said means for recompiling hazardous material and said components associated with hazard information is a rules engine for generating words and phrases used in the production of documents and system output.

5. The apparatus of claim 1 wherein said means for disseminating hazard information is a distribution module.

6. The apparatus of claim 1 wherein said means for disseminating hazard information is an on-line module.

7. The apparatus of claim 1 wherein said means for disseminating hazard information is a labeling module.

8. A data-centric hazard communication system comprising:
   a) an authoring module for entering information about a hazardous material and its characteristics;
   b) a module for selectively decompiling said hazardous material into its components and decomposition products and their respective characteristics;
   c) a rules engine operating on a set of user-defined rules for automatically associating said hazardous material characteristics and its component characteristics with user-defined hazard information for use in the production of documents and system output to provide hazard information about said hazardous material, its components, and substances related to said hazardous material; and
   d) a module for disseminating said hazard information about said hazardous material, its components, and substances related to said hazardous material wherein said module communicates with said authoring module.

9. The system of claim 8, wherein the module for decompiling the hazardous material includes an automated deblending module.

10. The system of claim 9, wherein the module for decompiling the hazardous material further includes a substance processor.

11. The system of claim 8, wherein the rules engine for associating said hazardous material characteristics and its component characteristics with user-defined hazard information further includes a user-defined set of hazardous material rules related to hazardous material and component characteristics.

12. The system of claim 8, wherein said hazard material rules may relate at least one regulatory, transportation, storage, handling, exposure, or emergency requirements for said hazardous material and its components.

13. The system of claim 8, wherein said user-defined hazardous material information is comprised of user-defined words and phrases.

14. The apparatus of claim 1, wherein said user defined set of hazardous material rules may relate to transportation, storage, regulatory, exposure or emergency requirements for said hazardous material and its components.

15. A method for communicating hazard information, the steps comprising:
   (a) entering information related to a hazardous material and its characteristics into a computerized database;
   (b) selectively automatically decompiling said hazardous material into its components, and decomposition products and their respective;
   (c) automatically associating said hazardous material and component characteristics with hazard information using a set of user defined hazardous material rules;
   (d) recompiling said hazardous material information associated with said hazardous material and its components; and
   (e) disseminating said hazardous material information related to said hazardous material and its components.

16. The method of claim 15, wherein step (b) further includes utilizing an automated deblender for decompiling said hazardous material.

17. The method of claim 16, wherein said automated deblender further includes a substance processor.

18. The method of claim 15, wherein said hazardous material rules includes rules relating at least one of regulatory, transportation, storage, handling, exposure or emergency requirements for said hazardous material and its components.

19. The method of claim 15, wherein step (e) further includes the step of automatically disseminating said hazard information online.

20. The method of claim 15, wherein step (e) further includes the step of creating hazardous material labels.

21. The method of claim 15, wherein said hazardous material and its components characteristics are referenced by a rules engine operating on user-defined rules to associate hazard information from a user-defined database of information with said hazardous material and its components.

22. The method of claim 15 wherein said hazard information is comprised of a user defined set of words and phrases.

* * * * *